US010720234B1

(12) United States Patent
Leonardi (10) Patent No.: US 10,720,234 B1
(45) Date of Patent: Jul. 21, 2020

(54) ACCOUNT RECONCILIATION BASED ON DISPENSING MEDICATION UNDER A DRUG DISCOUNT PROGRAM

(71) Applicant: Sentry Data Systems, Inc., Deerfield Beach, FL (US)

(72) Inventor: Travis Leonardi, Deerfield Beach, FL (US)

(73) Assignee: Sentry Data Systems, Inc., Deerfield Beach, FL (US)

( * ) Notice: Subject to any disclaimer, the term of this patent is extended or adjusted under 35 U.S.C. 154(b) by 833 days.

(21) Appl. No.: 14/559,556

(22) Filed: Dec. 3, 2014

Related U.S. Application Data (63) Continuation of application No. 14/498,524, filed on Sep. 26, 2014, now abandoned.

(51) Int. Cl.
*G16H 20/00* (2018.01)
*G06Q 30/02* (2012.01)
*G06Q 10/08* (2012.01)
*G06Q 30/04* (2012.01)

(52) U.S. Cl.
CPC ........... *G16H 20/00* (2018.01); *G06Q 10/083* (2013.01); *G06Q 30/0207* (2013.01); *G06Q 30/04* (2013.01)

(58) Field of Classification Search
CPC .. G06F 19/3462; G06Q 50/22; G06Q 10/083; G06Q 30/0207; G06Q 30/04; G16H 20/00
See application file for complete search history.

(56) References Cited

U.S. PATENT DOCUMENTS

| | | | |
|---|---|---|---|
| 2009/0326975 A1* | 12/2009 | Hardaway | G06Q 10/087 705/2 |
| 2011/0054935 A1* | 3/2011 | Hardaway | G06F 19/328 705/3 |
| 2013/0041675 A1* | 2/2013 | Cunningham | G06F 19/00 705/2 |
| 2015/0278924 A1* | 10/2015 | Maurer | G06Q 30/0635 705/26.81 |

OTHER PUBLICATIONS

Sample 340B Policy & Procedures Manual, Feb. 2014, Apexus, pp. 1-18.*

* cited by examiner

*Primary Examiner* — Christopher L Gilligan
(74) *Attorney, Agent, or Firm* — Loeb & Loeb LLP (57) ABSTRACT

A system, apparatus, and method are disclosed for account reconciliation based on dispensing medication under a drug discount program. The example embodiments may include receiving prescription claims that each identify a first medication being dispensed and an amount being dispensed. The example embodiments may further include identifying a subset of the prescription claims that are eligible for a drug discount program, aggregating the dispensation amounts to determine an aggregate amount of the first medication dispensed, instructing a distributor to credit a drug discount account of a covered entity in response to determining that the aggregate amount meets a dispensation requirement, and instructing a distributor to ship an amount of the first medication to a contract pharmacy.

3 Claims, 8 Drawing Sheets

Pharmacy Invoice # 17888

Bill to:
Medical Pharmacy
123 S. Main St.
Fake City, FL 12345

Revenue

From Patients    $ 7,952.53
From Insurance   $ 15,240.10

Total Revenue   $23,192.63

Disbursements

Pharmacy Fees            $ 6,562.00
Due to Covered Entity    $ 16,630.63

Total Disbursements    $ 23,192.63

ACCOUNT RECONCILIATION BASED ON DISPENSING MEDICATION UNDER A DRUG DISCOUNT PROGRAM

This application claims priority from and is a continuation of U.S. application Ser. No. 14/498,524 filed on Sep. 26, 2014, entitled "Account Reconciliation Based on Dispensing Medication Under a Drug Discount Program."

BACKGROUND

Field of the Invention

The invention relates to systems and methods for account reconciliation for parties involved with medication dispensation under a drug discount program. Among other fields and applications, the invention has utility in facilitating compliance with a drug discount program when dispensing prescription drugs.

Description of Related Art

The U.S. federal government provides a 340B Drug Pricing Program that enables certain eligible healthcare organizations, referred to as Covered Entities (CEs), to receive discounts on drug prices. The 340B program is designed to ease the financial burden on institutions that disproportionately serve patients who are unable to pay for services they receive. CEs may be nonprofit health care organizations that meet certain Federal designations or receive funding from specific Federal programs that can purchase discounted drugs through the 340B Program. Examples of CEs include Disproportionate Share Hospitals (DSH), Sole Community Hospitals (SCH), Rural Referral Centers (RRC), Critical Access Hospitals (CAH), Children's Hospitals, Free Standing Cancer Centers, Community Health Centers (CHC), and Federally Qualified Health Centers (FQHC).

The 340B program reduces the cost of goods (typically medications) for eligible Outpatient (OP) areas of a hospital. These price reductions typically result in savings on eligible OP pharmaceutical purchases. In some instances, a CE may contract with a pharmacy (contract pharmacy or CP), which dispenses medication for the CE. Cost savings under the 340B program result from discounts given by drug manufacturers, who offer reduced drug prices in order to participate in other government programs, such as drug reimbursement under Medicaid.

To benefit from the 340B program, CEs are required to follow stringent rules and regulations. For instance, to be a compliant eligible dispensation of medication and available for replenishment of the drug under the 340B program, the following conditions must be met: (1) the medication is dispensed to an outpatient of the CE; (2) the medication is dispensed in an eligible outpatient location, (3) the medication's 11-digit National Drug Code (NDC) at dispensation matches the NDC of the medication purchased from a wholesaler, (4) an eligible physician orders the dispensation, (5) the medication is provided for an eligible service, (6) data on the dispensation is tracked accurately and is available for auditing, and (7) the medication is dispensed to a patient for whom the covered entity maintains responsibility for care.

While there are many benefits to the 340B program, complying with the regulations can be difficult for CEs and CPs.

SUMMARY OF THE EXAMPLE EMBODIMENTS

The following presents a simplified summary of the present disclosure in order to provide a basic understanding of some aspects of the disclosure. This summary is not an extensive overview of the disclosure. It is not intended to identify key or critical elements of the disclosure or to delineate the scope of the disclosure. The following summary merely presents some concepts of the disclosure in a simplified form as a prelude to the more detailed description provided below.

A system, apparatus, computer readable media, and method are disclosed for account reconciliation based on dispensing medication under a drug discount program. The example embodiments may include receiving a plurality of prescription claims that each identify a first medication being dispensed and an amount of the first medication being dispensed, wherein each of the prescription claims is issued by one of a plurality of contract pharmacies of a pharmacy chain that has a relationship with a covered entity under a drug discount program. The example embodiments may further include identifying a subset of the prescription claims that are eligible for the drug discount program, aggregating the dispensation amounts of the prescription claims subset to determine an aggregate amount of the first medication dispensed to at least one patient by the plurality of contract pharmacies, instructing a distributor to credit a drug discount account of the covered entity in response to determining that the aggregate amount meets a dispensation requirement for the first medication under the drug discount program, and instructing a distributor to ship an amount of the first medication to at least one of the contract pharmacies.

BRIEF DESCRIPTION OF THE DRAWINGS

The invention may be better understood by references to the detailed description when considered in connection with the accompanying drawings. The components in the figures are not necessarily to scale, emphasis instead being placed upon illustrating the principles of the invention. In the figures, like reference numerals designate corresponding parts throughout the different views.

Persons of ordinary skill in the art will appreciate that elements in the figures are illustrated for simplicity and clarity so not all connections and options have been shown to avoid obscuring the inventive aspects. For example, common but well-understood elements that are useful or necessary in a commercially feasible embodiment are not often depicted in order to facilitate a less obstructed view of these various embodiments of the present disclosure. It will be further appreciated that certain actions and/or steps may be described or depicted in a particular order of occurrence while those skilled in the art will understand that such specificity with respect to sequence is not actually required. It will also be understood that the terms and expressions used herein are to be defined with respect to their corresponding respective areas of inquiry and study except where specific meanings have otherwise been set forth herein.

DETAILED DESCRIPTION

The present invention now will be described more fully with reference to the accompanying drawings, which form a part hereof, and which show, by way of illustration, specific exemplary embodiments by which the invention may be practiced. These illustrations and exemplary embodiments are presented with the understanding that the present disclosure is an exemplification of the principles of one or more inventions and is not intended to limit any one of the inventions to the embodiments illustrated. The invention may be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as methods, systems, computer readable media, apparatuses, or devices. Accordingly, the present invention may take the form of an entirely hardware embodiment, an entirely software embodiment, or an embodiment combining software and hardware aspects. The following detailed description is, therefore, not to be taken in a limiting sense.

Figure 1:
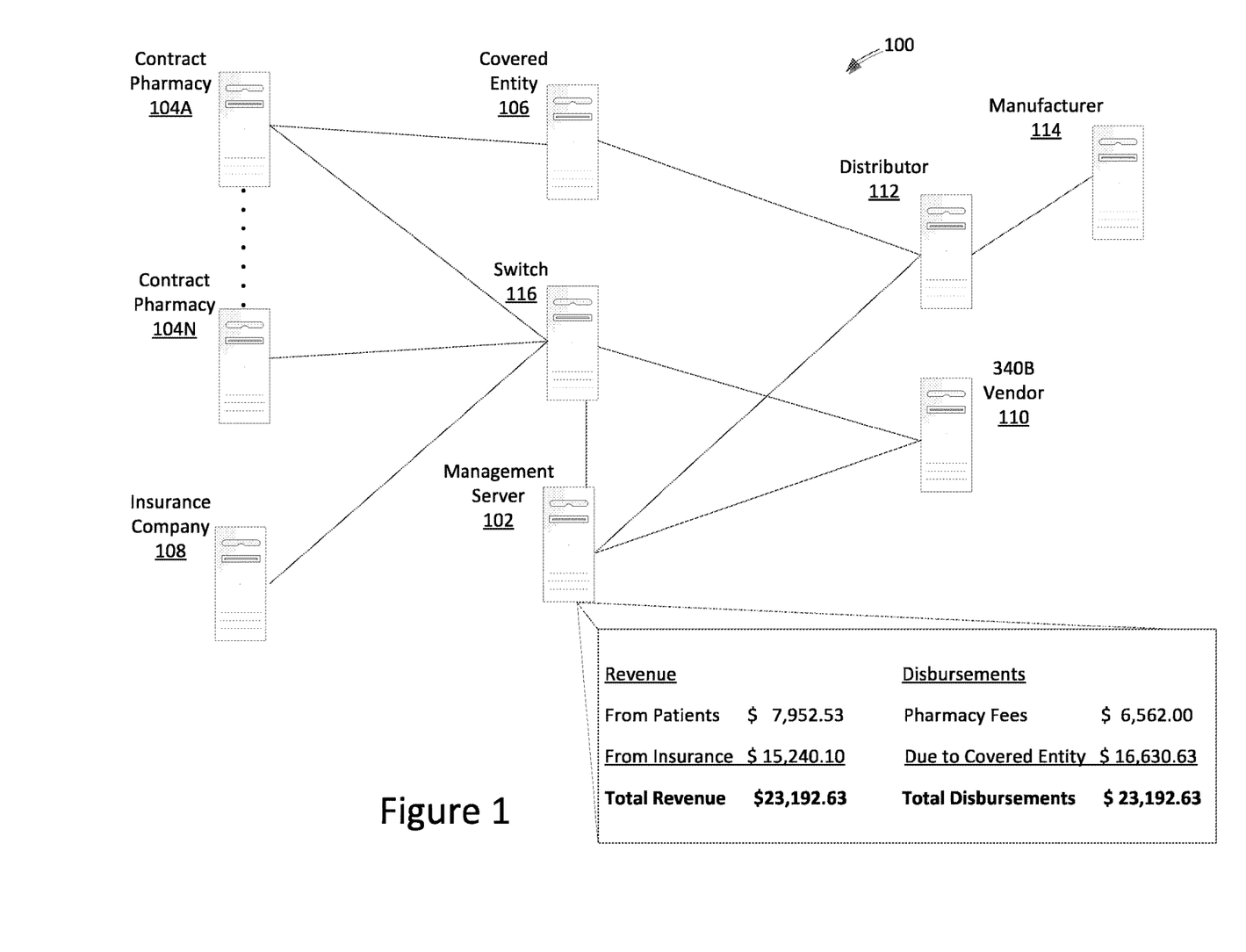
FIG. 1 shows a block diagram illustrating example aspects of a system for account reconciliation as part of drug dispensation in accordance with example embodiments.

FIG. 1 illustrates a block diagram of a system 100 in accordance with example embodiments. System 100 may provide an interface between covered entities (CEs), contract pharmacies (CPs), and distributors to facilitate account reconciliation and compliance with a drug discount program. The following describes the drug discount program as the U.S. Federal Government's 340B program. The concepts described herein, however, may be applied to any other drug discount program.

When the CE enrolls in the 340B program, a CE may set up a 340B account (e.g., a drug discount account) with a distributor that provides drugs eligible for replenishment under the 340B program. The CE purchases 340B drugs on behalf of the CP on the CE's 340B account. The CE may use the 340B account to purchase medication under the 340B program at a 340B price, which may be less than the wholesale price for the drug. Additionally, the CE may enter into contracts with CPs to dispense drugs for the CE under the 340B program. In an example, some of the CPs may be competitors of one another, and some may be part of a pharmacy chain. Each CP or CPs of a pharmacy chain may work with a same or different 340B vendor. When affiliated with a CE under the 340B program, the distributor may ship medication to the CP that dispensed a drug for the CE and met the requirements under the 340B program.

As depicted in FIG. 1, system 100 may include a switch 116 over which communication occurs between one or more CP computers 104A-N, a CE computer 106, an insurance company server 108, a 340B vendor server 110, a distributor server 112, and a manufacturer server 114. The switch 116 may be a relay or a server, or may represent a network, such as the Internet. A management server 102 may also receive some or all messages communicated via the switch 116, regardless of the actual final destination for a particular message. The management server 102 may be used to place orders and create invoices for the CP or CP chain.

The depicted servers and computers are illustrative and may be communicatively coupled by any type of network or combination of networks (e.g., local area network, wide area network, the Internet, and the like), and may support wired and/or wireless communication between any two devices. FIG. 1 depicts and illustrative numbers of devices. System 100, however, may include any number of computers and servers, as well as other components that are not shown. Any device shown in FIG. 1 may communicate with any other device, directly or indirectly.

Figure 2:
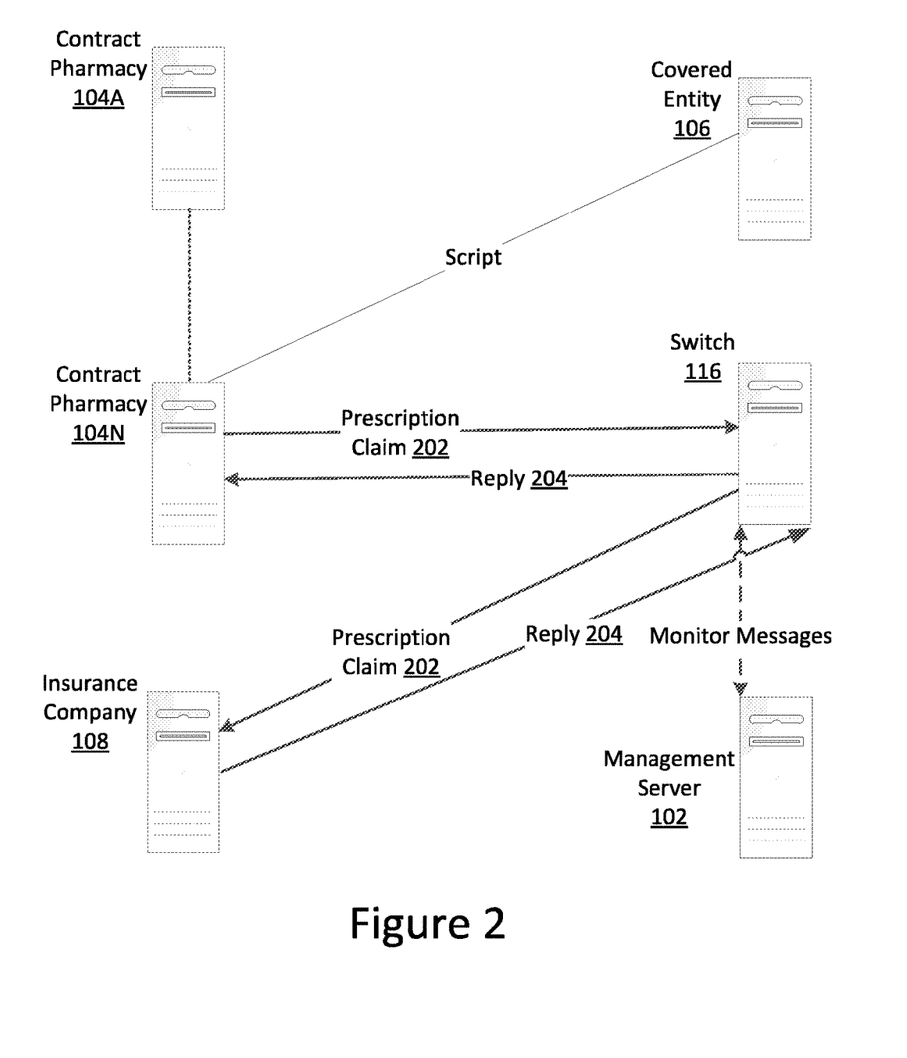
FIG. 2 illustrates a block diagram illustrating a prescription claim submission message flow for the system of FIG. 1 in accordance with example embodiments.

In an example embodiment, a doctor affiliated with a CE may issue a prescription to a patient. The prescription may be issued via a written prescription, telephone, or electronically through a computer, smart phone, tablet or other mobile device. The patient may proceed to a store location of a CP to have the prescription filled, or the prescription may be shipped directly to the patient's home. At the CP, a pharmacist may input the prescription information, including patient name, drug name, NDC, dose, quantity (e.g., amount of the drug being dispensed), prescribing physician, and the like, or the CP computer 104 may electronically retrieve the prescription and corresponding information from the CE server 106. With reference to FIG. 2, CP computer 104 may communicate a prescription claim message 202 to the switch 116, which is also received by management server 102. The prescription claim 202 may inform the management server 102 that a particular medication is being dispensed and optionally to seek payment from an insurance company.

The prescription claim 202 may include some or all of: prescription information (e.g., drug name, NDC number, etc.), a CP identifier (e.g., CP name, service provider identifier, etc.), a prescribing physician identifier, a covered entity identifier, and information on the patient's insurance plan, if any. The switch 116 may forward the prescription claim to insurance company server 108. The insurance server 108 may reply with a message 204 indicating whether the medication is covered under the patient's insurance plan and the amount the plan will pay. If the patient does not have insurance, this step may be skipped.

Regardless of whether the patient has insurance, CP computer 104 may communicate the prescription claim 202 to the management server 102 and 340B vendor 110 for determining eligibility under the drug discount program. Management server 102 obtains a 340B eligibility determination from 340B vendor 110. Management server 102 may coordinate with one or more 340B vendors of the CP's choosing for determining what prescription claims, if any, are eligible for the 340B program and which CE and CP will be awarded the prescription claims in the event of a "tie breaker" patient eligibility event. In an example, the 340B vendor 110 communicates 340B eligible claims to the management server 102 after or at the same time the CP is dispensing the medication. In another example, the management server 102 may wait to receive a predetermined number of prescription claims, or a predetermined amount of time (e.g., once an hour, once a day, twice a week, etc.), before inquiring whether any of the medication is eligible for the 340B program. In some examples, system 100 may include multiple 340B vendors that determine eligibility for respective CPs.

Figure 3:
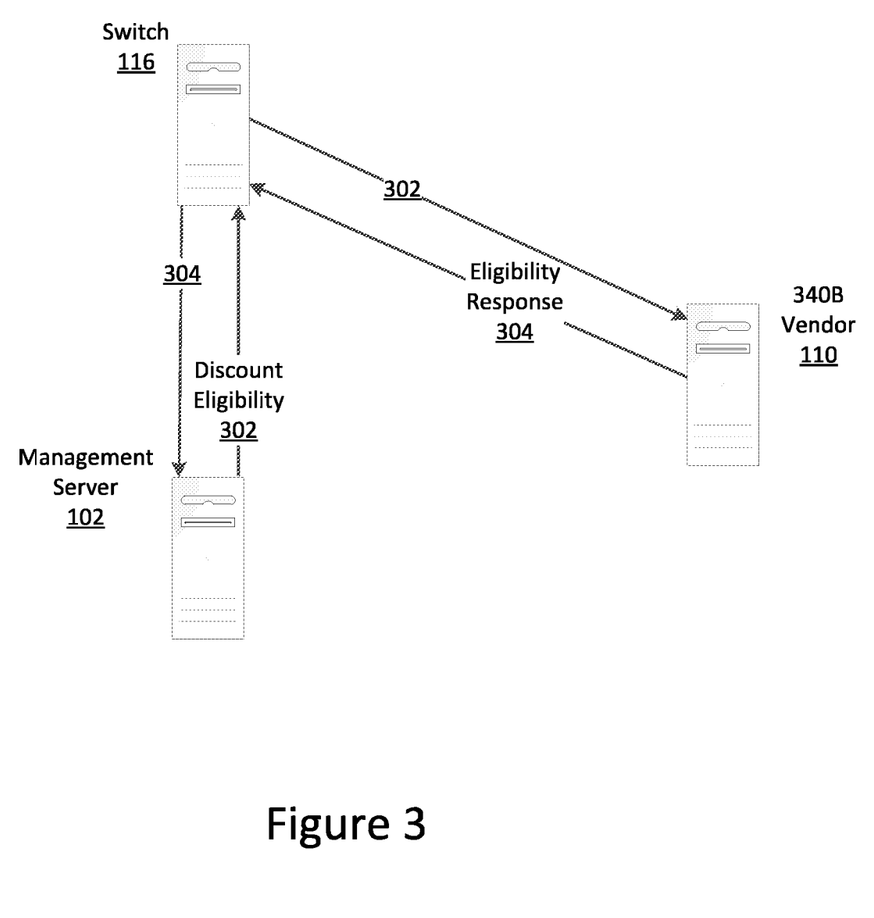
FIG. 3 illustrates a block diagram illustrating discount eligibility message flow for the system of FIG. 1 in accordance with example embodiments.

With reference to FIG. 3, the management server 102 may communicate to the 340B vendor server 110 a drug discount eligibility message 302 including a list of prescription claims received from a CP or CPs of a particular chain and the 340B vendor server may respond indicating which, if any, of the claims are eligible for the 340B program. The list of claims may include the drug NDC for each of medication listed in one of the prescription claims and may be the ones received within a predetermined time period. For example, the list of claims may be the ones issued by any CP of a particular pharmacy chain within the past 24 hours. In an example, the discount eligibility message 302 may be a pipe-delimited file communicated to the 340B vendor server via SSH File Transfer Protocol (SFTP). To determine which prescription claims are associated with a particular pharmacy chain, management server 102 may process CP identifiers in the prescription claims to determine with which pharmacy the CPs are affiliated (e.g., Walgreens, CVS, Target, etc.). Management server 102 may then determine which 340B vendor services that pharmacy chain, and send the discount eligibility message 302 to the server of that 340B vendor.

The 340B vendor server 110 may respond with an eligibility response message 304 indicating a subset of the list of prescription claims identifying which medication is eligible for 340B replenishment. The subset may identify as few as none, and up to all, of the list of prescription claims as being eligible. The 340B eligibility determination may be completed prior to, during, or after when the CP dispenses the medication to a patient. For each claim that is not eligible, the management server 102 may maintain a record of the non-eligibility.

For the eligible claims, the management server 102 may work with the CPs, CE, and distributor for reconciling the parties' accounts to reflect that the CEs are to only be charged the 340B price, instead of the wholesale price, to replenish the dispensed medication. This may involve at least three steps: (1) placing an order or credit for a quantity on a 340B account of the CE based on the difference between the wholesale price and the 340B price, (2) requesting that the CP pay the CE a contract price for replenishing the CP's inventory of the dispensed medication, and (3) shipping medication to the CP for inventory replenishment.

Figure 4:
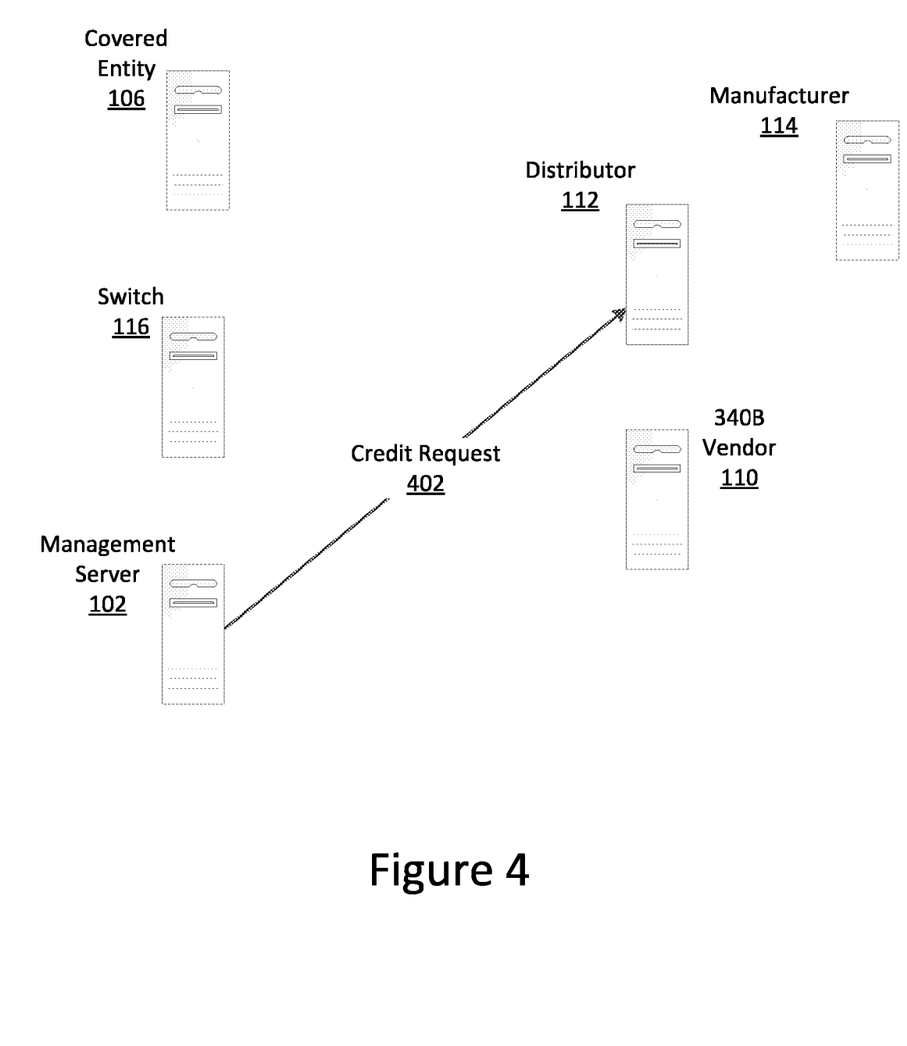
FIG. 4 illustrates a block diagram illustrating a credit request message flow for the system of FIG. 1 in accordance with example embodiments.

With reference to FIG. 4, management server 102 may instruct the distributor server 112 to credit the 340B account of the covered entity the difference between the wholesale price of the dispensed drug and the drug's 340B price (e.g., drug discount price). As depicted in FIG. 4, the management server 102 may communicate a credit request 402 to the distributor server 112. The credit request may identify the 340B eligible drug and quantity (e.g., submit the NDC and quantity). In response, the distributor server 112 may credit the 340B account. For example, a drug may cost $45 at wholesale, and the 340B price for that same drug may be $15. Thus, the distributor server 112 may apply a $30 credit to the CE's 340B account. The distributor server 112 optionally may communicate an acknowledgement message to the management server 102 indicating whether the 340B account was successfully credited.

Figure 5:
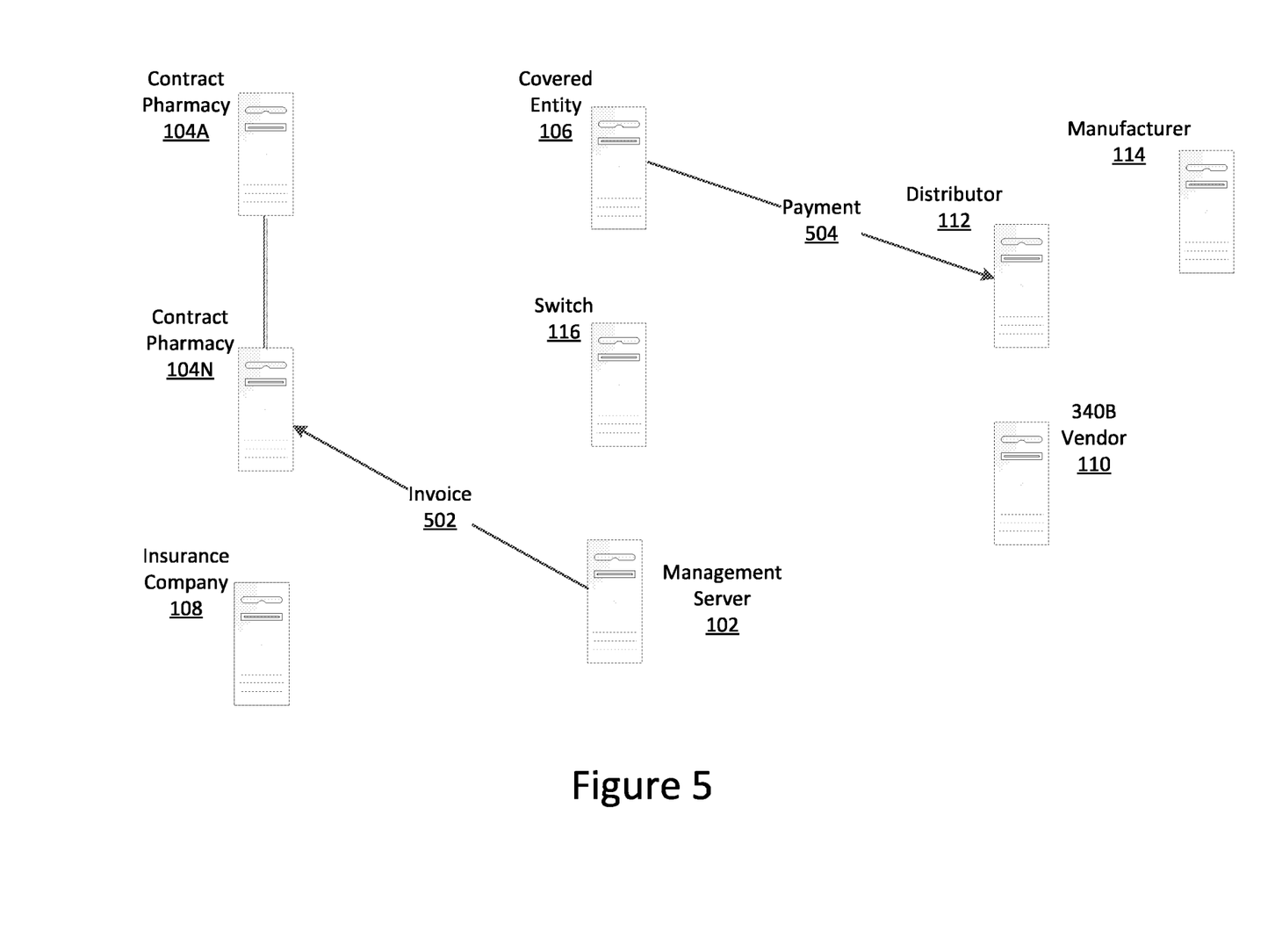
FIG. 5 illustrates a block diagram illustrating an invoice message flow for the system of FIG. 1 in accordance with example embodiments.

The CE and the CP may have a contractual relationship that specifies the dispensing fee to the CP. When a 340B eligible drug is dispensed, the management server 102 may communicate an invoice 502 to the CP computer 104, as depicted in FIG. 5. The invoice 502 may request that the CP pay some or all of the money the CP charged the patient and/or received from the insurance company for dispensing the 340B eligible drug less the dispensing fee kept by the CP.

Figure 6:
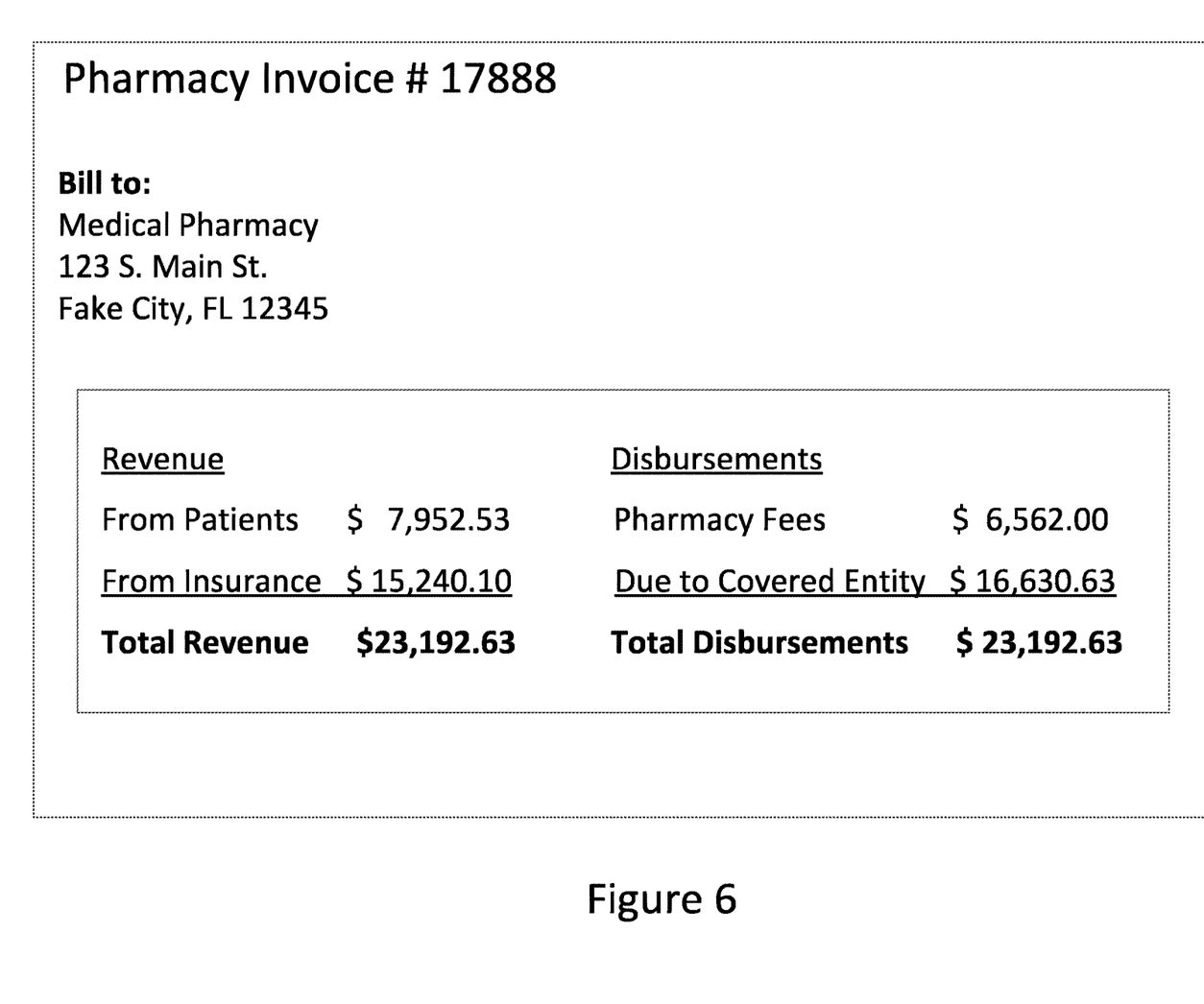
FIG. 6 illustrates an example invoice in accordance with example embodiments.

FIG. 6 illustrates an example invoice in accordance with example embodiments. As depicted, an invoice may identify the CP, revenue, and disbursement. Revenue may identify total amounts of money the CP collected from patients and collected from insurance plans for dispensing one or more medications. The depicted invoice is for multiple prescriptions that are 340B eligible, but the invoice may be for a single eligible 340B prescription. In the depicted example, fees collected from patients totals $7,952.53 and fees collected from insurance plans totals $15,240.10, for a total revenue of $23,196.63. Disbursement may identify total dispensation fees the pharmacy is permitted to keep from the revenue and the remainder is due to be paid to the CE, as specified in a contract between the CP and the CE. In the depicted example, pharmacy fees total $6,562.00 and total new billing totals $16,630.63, for a total disbursement of $23,196.63.

The amount invoiced for each drug may be based on a contract between the CE and the CP. In some examples, the amount may be less than the wholesale price of the drug, but greater than the 340B price. The amount the CP pays may be used, in part, to purchase the dispensed drug to replenish its inventory, and also to have the CE steer patients to the CP, instead of to a competing pharmacy.

With reference again to FIG. 5, to make payment, the CE server 106 may communicate payment message 504 for remitting payment to the distributor server 112, which may credit the 340B account of the CE. The distributor server 112 optionally may communicate an acknowledgement message to the management server 102 indicating whether payment was successfully received.

Figure 7:
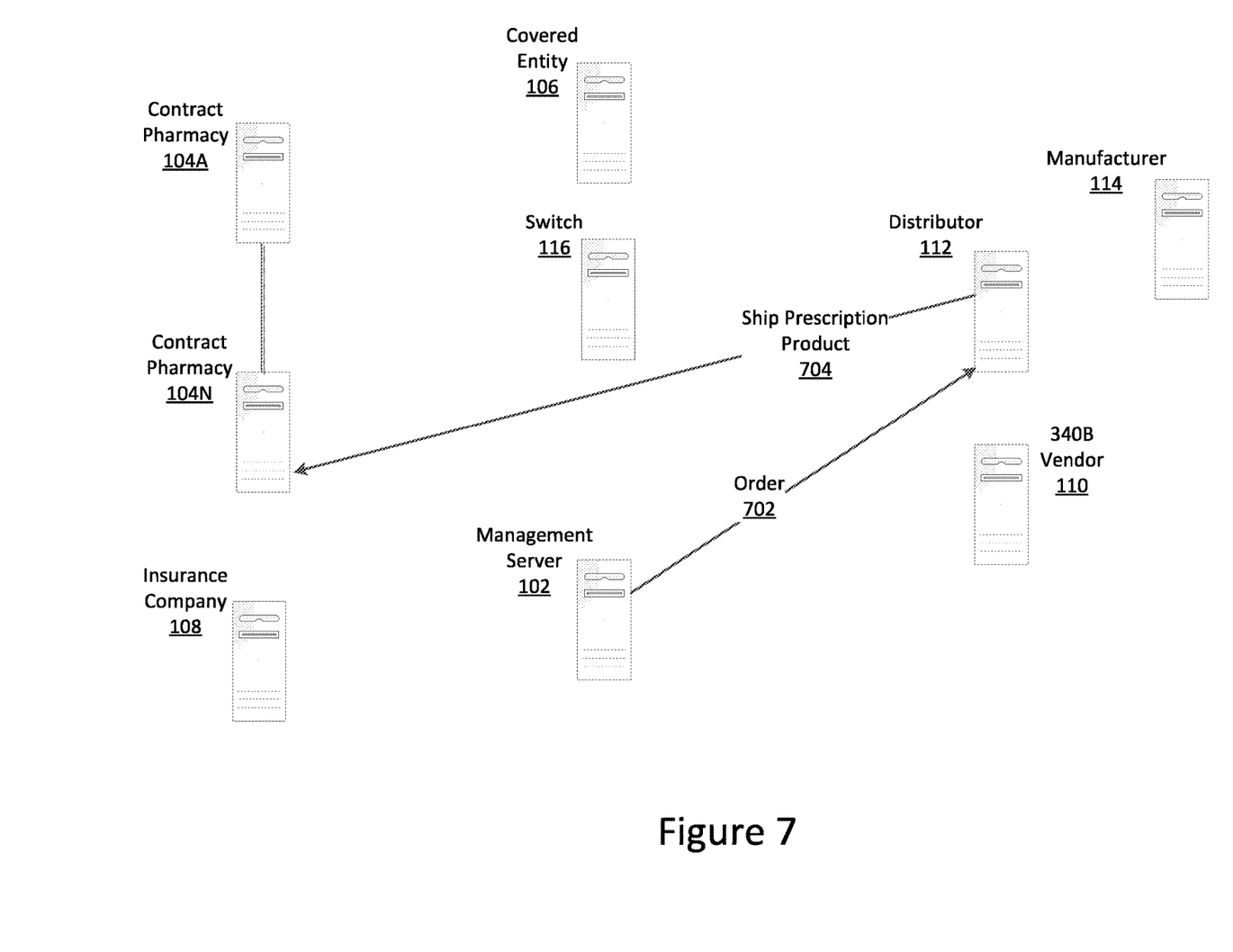
FIG. 7 illustrates a block diagram illustrating an order message flow for the system of FIG. 1 in accordance with example embodiments.

With reference to FIG. 7, the management server 102 may communicate an order 702 to the distributor server 112 for replenishing drugs dispensed by one or more CPs. The order 702 may identify the CP or pharmacy chain, the CE, the 340B eligible drug, the amount of the eligible drug being ordered (e.g., number of tablets), and the addresses of a CP pharmacy or CP pharmacies to where to ship the drugs. In response to receiving order 702, the distributor server 112 may debit the 340B price of the drug from the CE's 340B account and order shipment of the same drug the CP dispensed to the CE patient to replenish the CP's inventory.

Thus, the CE may realize savings under the 340B program and the CP's drug inventory may be replenished.

In some examples, the management server 102 may support aggregated ordering for multiple contract pharmacies associated with a particular pharmacy chain that has a relationship with a covered entity under the 340B program. As drugs are replenished under the 340B program in fixed amounts (e.g., multiples of 75 tables), management server 102 may maintain information on how many 340B eligible drugs have been dispensed by a CP alone and dispensed in aggregate by CPs of a pharmacy chain. As noted above, the 340B vendor server 110 may return a list of prescription claims indicating a subset of which are eligible under the 340B program. The management server 102 may aggregate the amounts of 340B eligible drugs dispensed by multiple CPs of the pharmacy chain to speed replenishment and invoicing for the chain. To do so, management server 102 may identify eligible prescription claims 202 having CP identifiers associated with a particular pharmacy chain. Management server 102 retrieve or have data on dispensation requirements for a particular drug to be eligible for replenishment under the 340B program. For example, a dispensation requirement may be that a particular drug can only be replenished under the 340B program in packages of 100 tablets, and thus a CP individually or a pharmacy chain collectively must dispense 100 tablets before the drug can be reordered under the 340B program. Management server 102 may also maintain data on the amounts of 340B eligible drugs that a CP has dispensed individually and collectively as part of a pharmacy chain. For example, a CP may have dispensed 30 tablets of a particular drug and the three store locations of CPs in a pharmacy chain associated with a CE may have collectively dispensed 120 tablets of the drug. Management server 102 may process the aggregate dispensation amounts to determine when the CP or pharmacy chain have met the dispensation requirements for a particular drug under the 340B program.

When met, management server 102 may generate and send the order 702 to the distributor server 112, as described above. The order 702 may request shipment of the particular drug to one or more CPs in the amount specified by the dispensation requirement (e.g., can replenish the drug under the 340B program in multiples of 100 tablets). If the order is for multiple CPs of a chain, order 702 may request that the distributor send the requested amount to each CP. For example, a first CP may dispense 30 tablets of a drug eligible for replenishment under the 340B program and a second CP may dispense 70 tablets of the same drug eligible for replenishment under the 340B program. The distributor may ship 30 tablets of the drug to the first CP, and 70 tablets to the second CP. In another example, order 702 may request that the distributor ship the drug to a distribution center of the chain for subdivision in any desired manner and shipment to the respective CPs. The order 702 may also request shipment of the medication to a particular one of the CPs, which will subdivide and ship the remainder to the other CPs for stock replenishment associated with a specific CE.

Thus, advantageously, system 100 can relieve the burden of a CP or CP chain from managing multiple 340B vendors, relieve the compliance burden on the CEs by allowing them to pick the 340B vendor of their choice, and reconcile accounts of the CP, CE, and distributor. Other advantages include that the accounts may be reconciled prior to or at the time drugs are dispensed, instead of having to manually reconcile after drug dispensation which may result in duplicate claims or other errors.

The example embodiments may be used in a number of additional implementations, including (1) managing drug inventory, (2) selecting which distributor to use, and (3) settling amounts owed in drugs.

In an example, the example embodiments may assist the distributor and/or manufacturer in inventory and manufacturing management. Management server 102 may maintain drug inventory data for one or more CP stores of one or more pharmacy chains. Based on this information, management server 102 may determine how much inventory of each drug is currently in stock at each CP store, and dispensation trends for each of the CP stores. For example, management server 102 may determine that the stores of a CP pharmacy chain have in aggregate 10,000 doses of drug ABC in the Miami, Fla. area, and that each CP store is dispensing on average 800 doses per day, thus the chain has a 12.5 day supply. Management server 102 may communicate data on the amount of a drug replenishable and on dispensation trends to the distributor server 112 and/or to the manufactures server 114. In some examples, distributor server 112 may use the data to automatically communicate an order to a manufacturer server 114 for one or more drugs and/or manufacturer server 114 may automatically cause shipment of drugs to the distributor based on current inventory levels and dispensation trends. In other examples, manufacturer server 114 may use the data to automatically schedule production for one or more drugs.

In another example, the example embodiments may select which distributor to use based on geographic location. Management server 102 may use dispensation trends, as discussed above, to determine a closest distributor that has a particular drug in a desired quantity available for shipment.

In a further example, the example embodiments may settle amounts owed in drugs, rather than in currency. For example, a CP may assess a dispensation fee that is deducted from the amount invoiced by the CE, as discussed above. Instead of keeping the dispensation fee, the CP may transfer the fee to the CE, which may order drugs for shipment to the CP at the 340B price or at a price below wholesale.

Figure 8:
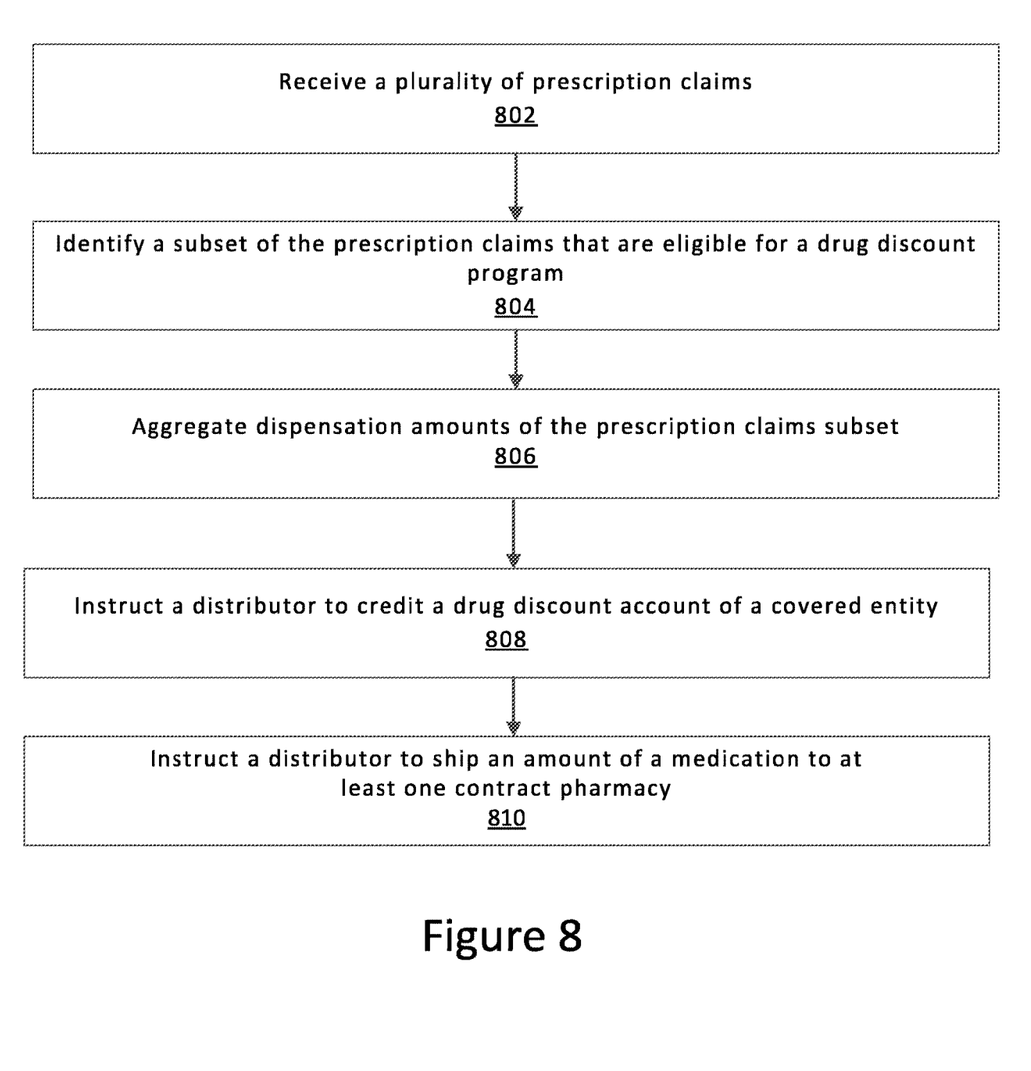
FIG. 8 illustrates a flow chart of an account reconciliation method in accordance with example embodiments.

FIG. 8 illustrates a flow chart of a method in accordance with example embodiments. The flow diagram may be implemented by a system or apparatus, such as, for example, management server 102. Each of the blocks shown in the flow diagram may be repeated one or more times, one or more of the blocks may be modified, and one or more of the blocks may be omitted. The method may be stored on a non-transitory computer readable medium as computer executable instructions. The computer executable instructions, when executed by at least one processor, may cause at least one computer or other device to perform the blocks as steps of a method one or more times. The flow diagram may begin at block 1002.

In block 802, the method may include receiving a plurality of prescription claims that each identify a first medication being dispensed and an amount of the first medication being dispensed, wherein each of the prescription claims is issued by one of a plurality of contract pharmacies of a pharmacy chain that has a relationship with a covered entity under a drug discount program.

In block 804, the method may include identifying a subset of the prescription claims that are eligible for the drug discount program.

In block 806, the method may include aggregating the dispensation amounts of the prescription claims subset to determine an aggregate amount of the first medication dispensed to at least one patient by the plurality of contract pharmacies.

In block 808, the method may include instructing a distributor to credit a drug discount account of the covered entity in response to determining that the aggregate amount meets a dispensation requirement for the first medication under the drug discount program.

In block 810, the method may include instructing a distributor to ship an amount of the first medication to at least one of the contract pharmacies. The amount shipped may be based on the amount each of the contract pharmacies dispensed that is eligible for replenishment under the 340B program (e.g., 30 dispensed, ship 30 for replenishment). For a pharmacy chain, any amount may be shipped to any pharmacy in the chain, regardless of whether the receiving pharmacy actually dispensed the drug.

The method in FIG. 8 may end, may repeat one or more times, or may return to any of the preceding blocks.

The computers and servers in FIG. 1 may be general purpose computers that may have, among other elements, a microprocessor (such as from the Intel Corporation, AMD or Motorola); volatile and non-volatile memory; one or more mass storage devices (i.e., a hard drive); various user input devices, such as a mouse, a keyboard, or a microphone; and a video display system. The computers and servers in FIG.

1 may be running on any one of many operating systems including, but not limited to WINDOWS, UNIX, LINUX, MAC OS, or Windows (XP, VISTA, etc.). It is contemplated, however, that any suitable operating system may be used for the present invention. The computers and servers in FIG. 1 may be a cluster of web servers, which may each be LINUX based and supported by a load balancer that decides which of the cluster of web servers should process a request based upon the current request-load of the available server(s).

The computers and servers in FIG. 1 are shown interconnected be lines. The lines may represent networks, including the Internet, WAN, LAN, Wi-Fi, other computer networks (now known or invented in the future), and/or any combination of the foregoing. It should be understood by those of ordinary skill in the art having the present specification, drawings, and claims before them that networks may connect the various components over any combination of wired and wireless conduits, including copper, fiber optic, microwaves, and other forms of radio frequency, electrical and/or optical communication techniques. It should also be understood that any network may be connected to any other network in a different manner. The interconnections between computers and servers in system 100 are examples. Any device depicted in FIG. 1 may communicate with any other device via one or more networks.

System 100 may include additional devices and networks beyond those shown. Further, the functionality described as being performed by one device may be distributed and performed by two or more devices. Multiple devices shown in FIG. 1 may also be combined into a single device, which may perform the functionality of the combined devices.

The various participants and elements described herein may operate one or more computer apparatuses to facilitate the functions described herein. Any of the elements in the above-described Figures, including any servers, user terminals, or databases, may use any suitable number of subsystems to facilitate the functions described herein.

Any of the software components or functions described in this application, may be implemented as software code or computer readable instructions that may be executed by at least one processor using any suitable computer language such as, for example, Java, C++, or Perl using, for example, conventional or object-oriented techniques.

The software code may be stored as a series of instructions or commands on a non-transitory computer readable medium, such as a random access memory (RAM), a read only memory (ROM), a magnetic medium such as a harddrive or a floppy disk, or an optical medium such as a CD-ROM. Any such computer readable medium may reside on or within a single computational apparatus and may be present on or within different computational apparatuses within a system or network.

It may be understood that the present invention as described above can be implemented in the form of control logic using computer software in a modular or integrated manner. Based on the disclosure and teachings provided herein, a person of ordinary skill in the art may know and appreciate other ways and/or methods to implement the present invention using hardware, software, or a combination of hardware and software.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention. A recitation of "a", "an" or "the" is intended to mean "one or more" unless specifically indicated to the contrary. Recitation of "and/or" is intended to represent the most inclusive sense of the term unless specifically indicated to the contrary.

One or more of the elements of the present system may be claimed as means for accomplishing a particular function. Where such means-plus-function elements are used to describe certain elements of a claimed system it will be understood by those of ordinary skill in the art having the present specification, figures and claims before them, that the corresponding structure is a general purpose computer, processor, or microprocessor (as the case may be) programmed to perform the particularly recited function using functionality found in any general purpose computer without special programming and/or by implementing one or more algorithms to achieve the recited functionality. As would be understood by those of ordinary skill in the art that algorithm may be expressed within this disclosure as a mathematical formula, a flow chart, a narrative, and/or in any other manner that provides sufficient structure for those of ordinary skill in the art to implement the recited process and its equivalents.

While the present disclosure may be embodied in many different forms, the drawings and discussion are presented with the understanding that the present disclosure is an exemplification of the principles of one or more inventions and is not intended to limit any one of the inventions to the embodiments illustrated.

The present disclosure provides a solution to the long-felt need described above. In particular, system 100 and the methods described herein may be configured to automatically perform account reconciliation and to facilitate compliance with a drug discount program. Further advantages and modifications of the above described system and method will readily occur to those skilled in the art. The disclosure, in its broader aspects, is therefore not limited to the specific details, representative system and methods, and illustrative examples shown and described above. Various modifications and variations can be made to the above specification without departing from the scope or spirit of the present disclosure, and it is intended that the present disclosure covers all such modifications and variations provided they come within the scope of the following claims and their equivalents.

What is claimed:

1. An apparatus comprising:
   at least one processor; and
   at least one memory storing instructions that, when executed by the at least one processor, cause the apparatus at least to perform:
   receiving, at a management server, a plurality of electronic prescription claims that each identify a first medication being dispensed and an amount of the first medication being dispensed, wherein each of the electronic prescription claims is issued by a plurality of covered pharmacy servers of a plurality of contract pharmacies of a pharmacy chain that has a relationship with a covered entity that issued a prescription of the plurality of electronic prescription claims to at least one patient under a drug discount program;
   sending, from the management server to a vendor server, a drug discount eligibility message including the plurality of electronic prescription claims;

receiving, at the management server and responsive to the drug discount eligibility message, an eligibility response message identifying a subset of the plurality of electronic prescription claims sent to the vendor server that are eligible for the drug discount program during the plurality of contract pharmacies of the pharmacy chain dispensing the first medication of at least one of the subset of the electronic prescription claims;

aggregating, by the management server, the dispensation amounts of the electronic prescription claims subset to determine an aggregate amount of the first medication dispensed by the plurality of contract pharmacies;

sending, from the management server to a distributor server, a credit request to credit a drug discount account of the covered entity in response to determining that the aggregate amount meets a dispensation requirement across the plurality of contract pharmacies for the first medication under the drug discount program;

sending, from the management server to the distributor server, an order to ship at least the aggregate amount of the first medication to at bast one of the contract pharmacies that dispensed the first medication, the order including a first amount of the aggregate amount for a first contract pharmacy and a second amount of the aggregate amount for a second contract pharmacy; and automatically invoicing, by the processor, funds respectively received by the plurality of contract pharmacies that each dispensed the first medication upon each respective contract pharmacy dispensing the first medication associated with the electronic prescription claims subset;

wherein an amount of the credit is based on a wholesale price of the first medication and a drug discount price of the first medication under the drug discount program.

2. A non-transitory computer readable medium storing processor-executable instructions that, when executed, cause an apparatus at least to perform:

receiving, at a management server, a plurality of electronic prescription claims that each identify a first medication being dispensed and an amount of the first medication being dispensed, wherein each of the electronic prescription claims is issued by a plurality of covered pharmacy servers of a plurality of contract pharmacies of a pharmacy chain that has a relationship with a covered entity that issued a prescription of the plurality of electronic prescription claims to at least one patient under a drug discount program;

sending, from the management server to a vendor server, a drug discount eligibility message including the plurality of electronic prescription claims;

receiving, at the management server and responsive to the drug discount eligibility message, an eligibility response message identifying a subset of the plurality of electronic prescription claims sent to the vendor server that are eligible for the drug discount program during the plurality of contract pharmacies of the pharmacy chain dispensing the first medication of at least one of the subset of the electronic prescription claims;

aggregating, by the management server, the dispensation amounts of the electronic prescription claims subset to determine an aggregate amount of the first medication dispensed by the plurality of contract pharmacies;

sending, from the management server to a distributor server, a credit request to credit a drug discount account of the covered entity in response to determining that the aggregate amount meets a dispensation requirement across the plurality of contract pharmacies for the first medication under the drug discount program;

sending, from the management server to the distributor server, an order to ship at least the aggregate amount of the first medication to the contract pharmacies that dispensed the first medication, the order including a first amount of the aggregate amount for a first contract pharmacy and a second amount of the aggregate amount for a second contract pharmacy; and automatically invoicing funds respectively received by the plurality of contract pharmacies that each dispensed the first medication upon each respective contract pharmacy dispensing the first medication associated with the electronic prescription claims subset;

wherein an amount of the credit is based on a wholesale price of the first medication and a drug discount price of the first medication under the drug discount program.

3. A processor-implemented method comprising:

receiving, at a management server, a plurality of electronic prescription claims that each identify a first medication being dispensed and an amount of the first medication being dispensed, wherein each of the electronic prescription claims is issued by a plurality of covered pharmacy servers of a plurality of contract pharmacies of a pharmacy chain that has a relationship with a covered entity that issued a prescription of the plurality of electronic prescription claims to at least one patient under a drug discount program;

sending, from the management server to a vendor server, a drug discount eligibility message including the plurality of electronic prescription claims;

receiving, at the management server and responsive to the drug discount eligibility message, an eligibility response message identifying a subset of the plurality of electronic prescription claims sent to the vendor server that are eligible for the drug discount program during the plurality of contract pharmacies of the pharmacy chain dispensing the first medication of at least one of the subset of the electronic prescription claims;

aggregating, by the management server, the dispensation amounts of the electronic prescription claims subset to determine an aggregate amount of the first medication dispensed by the plurality of contract pharmacies;

sending, from the management server to a distributor server, a credit request to credit a drug discount account of the covered entity in response to determining that the aggregate amount meets a dispensation requirement across the plurality of contract pharmacies for the first medication under the drug discount program;

sending, from the management server to the distributor server, an order to ship at least the aggregate amount of the first medication to the contract pharmacies that dispensed the first medication, the order including a first amount of the aggregate amount for a first contract pharmacy and a second amount of the aggregate amount for a second contract pharmacy; and automatically invoicing funds respectively received by the plurality of contract pharmacies that each dispensed the first medication upon each respective contract pharmacy dispensing the first medication associated with the electronic prescription claims subset;

wherein an amount of the credit is based on a wholesale price of the first medication and a drug discount price of the first medication under the drug discount program.

* * * * *